United States Patent [19]
Sanchez et al.

[11] Patent Number: 4,967,000
[45] Date of Patent: Oct. 30, 1990

[54] SPHERICAL NITROGUANIDINE PROCESS

[75] Inventors: John A. Sanchez; Edward L. Roemer; Lawrence A. Stretz, all of Los Alamos, N. Mex.

[73] Assignee: The United States of America as represented by the Department of Energy, Washington, D.C.

[21] Appl. No.: 406,010

[22] Filed: Sep. 12, 1989

[51] Int. Cl.$^5$ ............................................ C07C 277/08
[52] U.S. Cl. ..................................................... 564/242
[58] Field of Search ......................................... 564/242

[56] References Cited
U.S. PATENT DOCUMENTS
4,544,769 10/1985 Engel et al. ........................ 564/242

OTHER PUBLICATIONS
Feiser et al, "Reagents for Organic Synthesis", pp. 1109–1110 (1967).

Primary Examiner—James H. Reamer
Attorney, Agent, or Firm—Bruce H. Cottrell; Paul D. Gaetjens; William R. Moser

[57] ABSTRACT

A process of preparing spherical high bulk density nitroguanidine by dissolving low bulk density nitroguanidine in N-methyl pyrrolidone at elevated temperatures and then cooling the solution to lower temperatures as a liquid characterized as a nonsolvent for the nitroguanidine is provided. The process is enhanced by inclusion in the solution of from about 1 ppm up to about 250 ppm of a metal salt such as nickel nitrate, zinc nitrate or chromium nitrate, preferably from about 20 to about 50 ppm.

9 Claims, No Drawings

SPHERICAL NITROGUANIDINE PROCESS

This invention is the result of a contract with the Department of Energy (Contract No. W-7405-ENG-36).

FIELD OF THE INVENTION

The present invention relates to a process for the preparation of spherical high bulk density nitroguanidine.

BACKGROUND OF THE INVENTION

Nitroguanidine is used as a propellant and explosive. It has a greater detonation velocity and higher inherent density than that of trinitrotoluene (TNT), yet it is relatively impact insensitive. This combination of properties makes nitroguanidine an important material. Unfortunately, when nitroguanidine is crystallized from aqueous solutions during preparation and purification, it forms as long needles and has a resultant bulk density of only about 200 to 300 grams per liter (g/l). This is referred to as low bulk density nitroguanidine. While these long needles can be pulverized by grinding, the bulk density is not greatly increased by such mechanical processing.

U.S. Pat. No. 4,544,769 describes a process of preparing compact or high bulk density nitroguanidine by recrystallization from an initially hot nitroguanidine solution, wherein the solvent for the nitroguanidine is selected from the group of: (i) polyhydric, lower aliphatic alcohols; (ii) mono- or dialkyl ethers of polyhydric, lower aliphatic alcohols; (iii) dimethylformamide; (iv) dimethyl sulfoxide; and, (v) mixtures thereof. The disclosure indicates that bulk densities of from 900 to 1020 g/l are obtained in this process. However, repeated efforts by the present inventors to duplicate these results failed leading them to seek an alternative method of preparing high bulk density nitroguanidine from low bulk density nitroguanidine.

Accordingly, it is an object of this invention to provide a process of preparing spherical high bulk density nitroguanidine having a density of from about 900 to 1100 g/l from low bulk density nitroguanidine.

SUMMARY OF THE INVENTION

To achieve the foregoing and other objects, extensive efforts were undertaken to develop the desired process. In accordance with the purposes of the present invention, as embodied and broadly described herein, the present invention provides a process of preparing spherical high bulk density nitroguanidine including: dissolving low bulk density nitroguanidine in a solvent of N-methyl pyrrolidone at elevated temperatures of, e.g., from about 55°C. to about 120°C.; cooling the solution to lower temperatures of, e.g., from about 0°C. to about 70°C., as a liquid characterized as essentially a nonsolvent for the nitroguanidine is added to the solution; and, separating spherical high bulk density nitroguanidine from the solution. In a preferred embodiment, a metal salt, e.g., nickel nitrate, zinc nitrate or chromium nitrate, preferably nickle nitrate, is included in the N-methyl pyrrolidone solvent at concentrations of from about 1 parts per million (ppm) to about 250 ppm of metal salt preferably from about 20 to about 50 ppm thereby enhancing formation of spherical high bulk density nitroguanidine.

DETAILED DESCRIPTION

The present invention concerns the preparation of spherical high bulk density nitroguanidine. Low bulk density nitroguanidine is readily available, but is unsuitable for processing as a propellant or explosive.

The present process initially involves dissolving low bulk density nitroguanidine having, e.g., a density of less than 900 g/l, more usually from about 200 to about 300 g/l, in N-methyl pyrrolidone at elevated temperatures. By "elevated temperatures" is meant temperatures whereat nitroguanidine will be readily dissolved in the solvent at concentrations of up to about 300 grams of nitroguanidine per liter of N-methyl pyrrolidone. Generally, such elevated temperatures will be from about 55°C. to about 120°C., preferably from about 55°C. to about 90°C. Above about 120°C., decomposition of the nitroguanidine can occur.

The hot solution of nitroguanidine is then cooled to lower temperatures as a liquid characterized as essentially a nonsolvent for the nitroguanidine is added. By "lower temperatures" is meant temperatures whereat addition of the nonsolvent will precipitate nitroguanidine from the solution. Generally, such lower temperatures will be from about 0°C. to about 70°C., preferably from about 20°C. to about 50°C. The hot solution can be cooled by addition of the nonsolvent at an appropriate temperature less than that of the hot solution or by other suitable process heat transfer techniques. Optionally, the nonsolvent liquid can be added to the hot solution without attaining the desired lower temperatures and the resulting combination then cooled to the lower temperatures.

The nonsolvent for the nitroguanidine can be selected from the group consisting of methanol, ethanol, acetone, tetrahydrofuran, chloroform, carbon tetrachloride or methyl ethyl ketone. Preferably, the nonsolvent is acetone or methyl ethyl ketone and more preferably the nonsolvent is acetone as it is easier to recover and recycle from the N-methyl pyrrolidone. The amount of nonsolvent added to the solution of nitroguanidine is generally about 1 liter of nonsolvent per 400 grams of solution.

In the preferred practice of the present invention, a metal salt is included with the N-methyl pyrrolidone. The metal salt can be, e.g., nickel nitrate, zinc nitrate or chromium nitrate, although nickel nitrate is preferred. The metal salt can be added in amounts of from about ppm to about 250 ppm, preferably from about 20 to about 50 ppm.

After cooling the hot nitroguanidine solution to the lower temperatures by addition of the metal salt and nonsolvent, the admixture can be maintained at the lower temperature until precipitation of the nitroguanidine is complete. The crystals can then be separated from the liquid by any suitable means, e.g., by filtering, decantation, or centrifugation, washed and dried.

The present invention is more particularly described in the following example which is intended as illustrative only, since numerous modifications and variations will be apparent to those skilled in the art.

EXAMPLE 1

Into 20 ml of N-methyl pyrrolidone including 30 ppm nickel as nickel nitrate at about 55°C. was dissolved 5.75 g of low density nitroguanidine having a density of from about 100 to about 200 g/l. The solution was then cooled to by succesive additions of room temperature (about 20°C.) acetone. First, 20 ml of acetone was added with agitation. After two minutes, another 20 ml of acetone was added, and after another two minutes an additional 25 ml of acetone was added. The admixture was held for five minutes, after which the crystals of nitroguanidine were separated by vacuum-filtration, washed in acetone and dried. The resultant product of spherical particles had a density of 1030 g/1 with a 57% yield.

Although the present invention has been described with reference to specific details, it is not intended that such details should be regarded as limitations upon the scope of the invention, except as and to the extent that they are included in the accompanying claims.

What is claimed is:

1. A process for the preparation of spherical high bulk density nitroguanidine comprising:
   a. dissolving low bulk density nitroguanidine in N-methyl pyrrolidone at temperature of from about 55°C. to about 120°C.;
   b. cooling the solution of nitroguanidine in N-methyl pyrrolidone to temperatures from about 0° about 70° as a liquid characterized as a nonsolvent for nitroguanidine is added to the solution; and,
   c. separating spherical high bulk density nitroguanidine from the solution.

2. The process of claim 1 wherein the liquid nonsolvent is acetone.

3. The process of claim 1 wherein a metal salt selected from the group consisting of nickel nitrate, zinc nitrate and chromium nitrate is included in the N-methyl pyrrolidone at levels of up to 250 ppm.

4. The process of claim 1 wherein the solution of nitroguanidine in N-methyl pyrrolidone is cooled by addition of the liquid nonsolvent.

5. The process of claim 4 wherein the liquid nonsolvent is acetone.

6. The process of claim 5 wherein a metal salt selected from the group consisting of nickel nitrate, zinc nitrate and chromium nitrate is included in the N-methyl pyrrolidone.

7. The process of claim 6 wherein the included metal salt is nickel nitrate.

8. The process of claim 6 wherein the metal salt is included in amounts of from about 20 to about 50 ppm.

9. The process of claim 1 wherein the solution of nitroguanidine in N-methyl pyrrolidone is cooled to temperatures from about 20°C. to about 50°C. as the nonsolvent liquid is added.

* * * * *